(12) United States Patent
Nakayama et al.

(10) Patent No.: US 9,700,243 B2
(45) Date of Patent: Jul. 11, 2017

(54) RESPIRATORY STATE ESTIMATION DEVICE, METHOD, AND STORAGE MEDIUM

(71) Applicant: Kabushiki Kaisha Toshiba, Minato-ku, Tokyo (JP)

(72) Inventors: Kanako Nakayama, Tokyo (JP); Junya Takakura, Kanagawa (JP); Sawa Fuke, Kanagawa (JP); Yasunobu Yamauchi, Kanagawa (JP)

(73) Assignee: TDK Corporation, Tokyo (JP)

( * ) Notice: Subject to any disclaimer, the term of this patent is extended or adjusted under 35 U.S.C. 154(b) by 102 days.

(21) Appl. No.: 14/753,865

(22) Filed: Jun. 29, 2015

(65) Prior Publication Data

US 2015/0374265 A1   Dec. 31, 2015

(30) Foreign Application Priority Data

Jun. 30, 2014   (JP) ................. 2014-134471

(51) Int. Cl.
*A61B 5/00* (2006.01)
*A61B 5/113* (2006.01)
(Continued)

(52) U.S. Cl.
CPC ............. *A61B 5/113* (2013.01); *A61B 5/024* (2013.01); *A61B 5/0205* (2013.01);
(Continued)

(58) Field of Classification Search
CPC .... A61B 2562/0204; A61B 2562/0219; A61B 5/0205; A61B 5/024; A61B 5/02438;
(Continued)

(56) References Cited

U.S. PATENT DOCUMENTS 8,103,333 B2 *   1/2012   Tran .................... A61B 5/0022
                                                                     600/509
2009/0062628 A1   3/2009   Yamamoto et al.

FOREIGN PATENT DOCUMENTS

EP   2653108 A1   10/2013
JP   3543392 B2   7/2004
(Continued)

OTHER PUBLICATIONS

EPO Search Report dated Sep. 25, 2015, in Application No. EP 15174621.1-1657, 9 pages.

*Primary Examiner* — George Manuel
(74) *Attorney, Agent, or Firm* — Finnegan, Henderson, Farabow, Garrett & Dunner, LLP (57) ABSTRACT

According to one embodiment, a respiratory measurement module measures a first signal related to a respiratory fluctuation of the user. A body movement measurement module measures a second signal related to a movement of a trunk of the user. A respiration detector detects whether or not the user is in a respiratory arrest state, based on the measured first signal measured. A body movement detector detects whether or not the trunk of the user is moving, based on the measured second signal. An estimation module estimates a respiratory state of the user, based on a detection result by the respiration detector and a detection result by the body movement detector. An output module outputs respiratory state information indicating the estimated respiratory state.

11 Claims, 7 Drawing Sheets

(51) Int. Cl.
  *A61B 5/0205* (2006.01)
  *A61B 5/024* (2006.01)
  *A61B 5/0402* (2006.01)
  *A61B 5/08* (2006.01)
  *A61B 5/1455* (2006.01)

(52) U.S. Cl.
  CPC ........ *A61B 5/02438* (2013.01); *A61B 5/0402* (2013.01); *A61B 5/08* (2013.01); *A61B 5/0803* (2013.01); *A61B 5/0826* (2013.01); *A61B 5/1135* (2013.01); *A61B 5/14552* (2013.01); *A61B 5/4818* (2013.01); *A61B 5/721* (2013.01); *A61B 2562/0204* (2013.01); *A61B 2562/0219* (2013.01)

(58) Field of Classification Search
  CPC ....... A61B 5/0402; A61B 5/08; A61B 5/0803; A61B 5/0826; A61B 5/113; A61B 5/1135; A61B 5/14552; A61B 5/4818; A61B 5/721
  See application file for complete search history.

(56) References Cited

FOREIGN PATENT DOCUMENTS

| | | |
|---|---|---|
| JP | 2006-061201 A | 3/2006 |
| JP | 2010-082226 A | 4/2010 |
| JP | 2011-182919 | 9/2011 |
| JP | 2014-8160 | 1/2014 |
| WO | WO 2005/044090 A2 | 5/2005 |

* cited by examiner

| Date | Time | Respiratory arrest period | Movement of chest | Attitude |
|---|---|---|---|---|
| 2014/06/15 | 2:20 | 1m9s | Yes | Supine position |
| ⋮ | ⋮ | ⋮ | ⋮ | ⋮ |

| Date | Number of respiration arrests | Movement of chest |
|---|---|---|
| 2014/06/15 | 35 | 97% |
| 2014/06/16 | 30 | 96% |
| ⋮ | ⋮ | ⋮ |

RESPIRATORY STATE ESTIMATION DEVICE, METHOD, AND STORAGE MEDIUM

CROSS-REFERENCE TO RELATED APPLICATIONS

This application is based upon and claims the benefit of priority from Japanese Patent Application No. 2014-134471, filed Jun. 30, 2014, the entire contents of which are incorporated herein by reference.

FIELD

Embodiments described herein relate generally to a respiratory state estimation device, a method, and a storage medium.

BACKGROUND

In recent years, sleep apnea syndrome (SAS), wherein respiration cannot be performed during sleep, is known as a pathology related to respiration during sleep.

The diagnosis of sleep apnea syndrome is generally made by a doctor, etc., after an all-night polysomnography (PSG) test in, for example, a hospital has been conducted.

However, the PSG test is a large burden on a patient who takes the test, because it requires the patient to wear, for example, a band for measuring movement of the abdomen, on the abdomen, etc., and to sleep with a sensor for measuring nasal respiration inserted in the nose. Furthermore, a burden is also placed on the hospital where the PSG test is conducted.

Therefore, there have been conducted simple tests in which arterial blood oxygen saturation or nasal respiration is measured by, for example, a device (sensor) which can be easily attached to the patient, whereby a respiratory arrest state (apnea state) of the patient is estimated.

It should be noted that sleep apnea syndrome, described above, is mainly classified into obstructive SAS (OSAS), wherein an airway is obstructed and so respiration is arrested, and central SAS (CSAS), wherein a respiration command from the brain is not issued and so respiration is arrested. Obstructive SAS and central SAS differ in treatment, and thus need discrimination from each other.

However, in the above-described simple tests, obstructive SAS and central SAS cannot be discriminated from each other. It is therefore desired that even a simple test conducted by a device which can be easily attached to a patient provide information helpful in discriminating between obstructive SAS and central SAS (that is, information helpful in the diagnosis of sleep apnea syndrome).

DETAILED DESCRIPTION

Various embodiments will be described hereinafter with reference to the accompanying drawings.

In general, according to one embodiment, a respiratory state estimation device attached to a user during sleep when used is provided. The device includes a respiratory measurement module, a body movement measurement module, a respiration detector, a body movement detector, an estimation module and an output module. The respiratory measurement module is configured to measure a first signal related to a respiratory fluctuation of the user. The body movement measurement module is configured to measure a second signal related to a movement of a trunk of the user. The respiration detector is configured to detect whether or not the user is in a respiratory arrest state, based on the first signal measured by the respiratory measurement module. The body movement detector is configured to detect whether or not the trunk of the user is moving, based on the second signal measured by the body movement measurement module. The estimation module is configured to estimate a respiratory state of the use based on a detection result by the respiration detector and a detection result by the body movement detector. The output module is configured to output respiratory state information indicating the estimated respiratory state.

Figure 1:
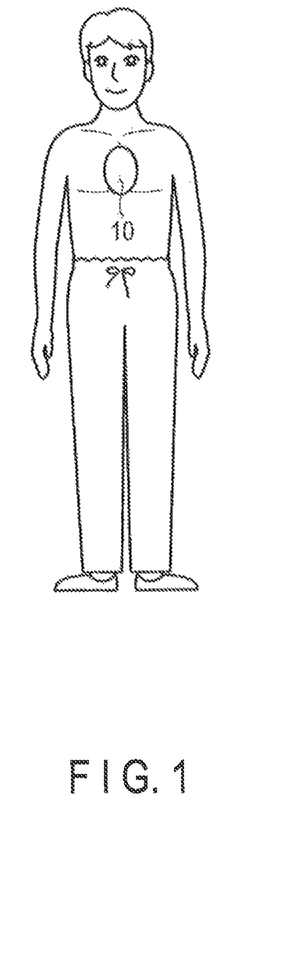
FIG. 1 is an illustration showing an example of use of a respiratory state estimation device according to an embodiment.

FIG. 1 shows an example of use of a respiratory state estimation device according to an embodiment. A respiratory state estimation device 10 shown in FIG. 1 is a small, lightweight and thin device, and is used by attaching an attachment surface of the respiratory state estimation device 10 to the chest, etc., of a user during sleep with, for example, an elastic gel pad or an adhesive tape. The respiratory state estimation device 10 has a shape similar to, for example, an ellipse or a rectangle, to be easily attached to the vicinity of the center of the chest.

The respiratory state estimation device 10 according to the embodiment includes a sensor (hereinafter, referred to as a respiratory measurement sensor) which measures a signal (first signal) related to a respiratory fluctuation of the user and a sensor (hereinafter, referred to as a body movement measurement sensor) which measures a signal (second signal) related to a movement of the trunk (for example, a movement of the chest) of the user, as will be described later. The respiratory state estimation device 10 according to the embodiment is used to estimate a respiratory state of the user during sleep, using the respiratory measurement sensor and the body movement measurement sensor.

Figure 2:
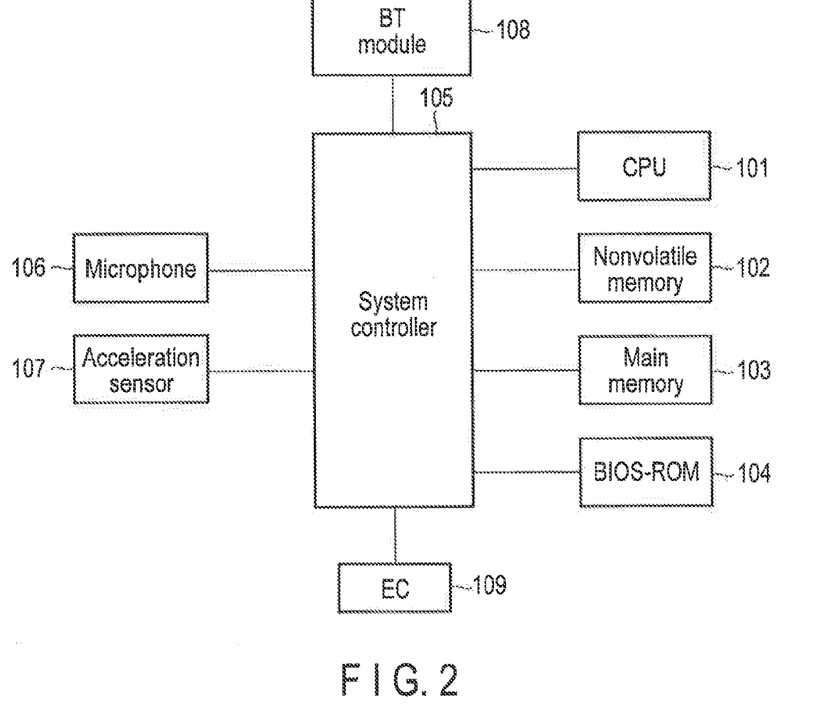
FIG. 2 is an illustration showing an example of a system configuration of the respiratory state estimation device shown in FIG. 1.

FIG. 2 is an illustration showing a system configuration of the respiratory state estimation device 10 shown in FIG. 1. As shown in FIG. 2, the respiratory state estimation device 10 includes a CPU 101, a nonvolatile memory 102, a main memory 103, a BIOS-ROM 104, a system controller 105, a microphone 106, an acceleration sensor 107, a BT module 108, an EC 109, etc.

The CPU 101 is a processor which controls operation of each component in the respiratory state estimation device 10. The CPU 101 executes various kinds of software loaded from the nonvolatile memory 102, which is a storage device, to the main memory 103.

The CPU 101 also executes a Basic Input/Output System (BIOS) stored in the BIOS-ROM 104. The BIOS is a program for hardware control.

The system controller 105 is a bridge device which connects the CPU 101 and various components. The CPU 101, the nonvolatile memory 102, the main memory 103, the BIOS-ROM 104, the microphone 106, the acceleration sensor 107. The ET module 108, the PC 109, etc., are connected to the system controller 105.

The microphone 106 is a sensor used as the above-described respiratory measurement sensor, and measures a sound signal indicating an internal sound, or an external sound of the user. The sound signal measured by the microphone 106 is, for example, a signal indicating a respiratory sound produced in accordance with the user's respiration (hereinafter, referred to as a respiratory sound signal).

The acceleration sensor 107 is a sensor used as the above-described body movement measurement sensor, and measures an acceleration signal indicating acceleration which acts on the respiratory state estimation device 10. The acceleration indicated by the acceleration signal measured by the acceleration sensor 107 is acceleration produced by a movement of the trunk (that is, a body movement) of the user, acceleration due to gravity, etc. In addition, the acceleration sensor 107 is, for example, a triaxial acceleration sensor (three-dimensional acceleration sensor) which can detect an acceleration signal in each axial direction of orthogonal three axes (x-, y- and z-axes).

The PT module 108 is a module configured to wirelessly communicate with a Bluetooth-enabled device through Bluetooth (registered trademark). The Bluetooth-enabled device is, for example, a smartphone, a tablet computer, or a personal computer (PC).

The EC 109 is a power management controller for performing power management of the respiratory state estimation device 10.

Although omitted in FIG. 2, the respiratory state estimation device 10 according to the embodiment may be provided with various kinds of sensor which can measure, for example, an electrocardiographic waveform (electrocardiogram), a pulse waveform, and arterial blood oxygen saturation, except for the microphone 106 and the acceleration sensor 107, which have been described above.

In this manner, the respiratory state estimation device 10 includes sensors in its housing. Because the sensors have analog front-ends differing in specification from sensor to sensor, both flexibility and high performance are required, which may lead to an increase in size. In the embodiment, however, a module several millimeters square can be realized by integrating the analog front-ends, the CPU 101, etc., on a single chip by pseudo-SoC technology. Pseudo-SoC technology is a technology which allows both a reduction in size corresponding to that of an SoC and a degree of freedom in design corresponding to that of an SiP by integrating components on a wafer. The respiratory state estimation device 10, which is small, lightweight (approximately several tens of grams), and thin (approximately several millimeters) can be realized by connecting a few peripheral components such as an antenna and a battery to the module. Although it has been herein explained that the respiratory state estimation device 10 can be reduced in size by pseudo-SoC technology, the respiratory state estimation device 10 can also be reduced in size by, for example, an LSI.

It is assumed that the respiratory state estimation device 10 according to the embodiment is used, for example, when a doctor, etc., makes a diagnosis of sleep apnea syndrome as a pathology related to respiration during sleep. Sleep apnea syndrome is classified into obstructive SAS, wherein an airway is obstructed during sleep and so respiration is arrested, and central SAS, wherein a respiration command from the brain is not issued and so respiration is arrested.

In obstructive SAS, respiration are impossible because of airway obstruction. Thus, in a respiratory arrest (oral and nasal respiratory arrest) state, it can be perceived that the chest and the abdomen make a respiratory movement for supplementing the amount of respiration which is lessened by the respiratory arrest, that is, a respiratory movement in the respiratory arrest state (hereinafter, referred to as labored respiration). On the other hand, in central SAS, crib cage and an abdominal wall make no movement because of the loss of output from the respiratory center to a respiratory muscle, and thus, labored respiration cannot be perceived.

It is therefore helpful in discriminating between obstructive SAS and central SAS, described above, to give information which allows a doctor, etc., to ascertain whether or not the user is in a labored respiratory state during a sleeping period. Thus, in the embodiment, a function of estimating a respiratory state of the user with the respiratory measurement sensor (the microphone 106) and the body movement measurement sensor the acceleration sensor 107) is provided to give information helpful in discriminating between obstructive SAS and central SAS.

Figure 3:
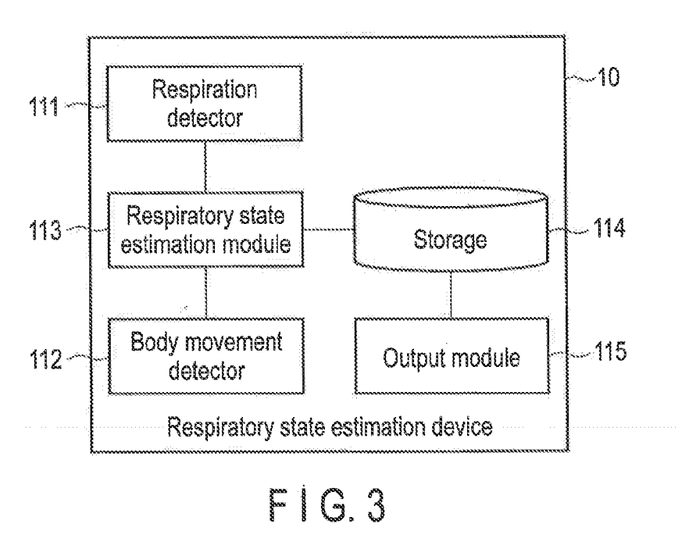
FIG. 3 is a block diagram mainly showing an example of a functional configuration of the respiratory state estimation device according to the embodiment.

FIG. 3 is a block diagram mainly showing a functional configuration of the respiratory state estimation device 10 according to the embodiment. As shown in FIG. 3, the respiratory state estimation device 10 includes a respiration detector 111, a body movement detector 112, a respiratory state estimation module 113, a storage 114, and an output module 115.

The respiration detector 111 detects whether or not the user is in a respiratory arrest state, based on a sound signal measured by the microphone 106.

The body movement, detector 112 detects whether or not the trunk of the user is moving, based on an acceleration signal measured by the acceleration sensor 107. When the respiratory state estimation device 10 is attached to the chest of the user as described above, the body movement detector 112 detects whether or not the chest of the user is moving mainly accompanying respiration, as a movement of the trunk of the user.

The respiratory state estimation module 113 estimates a respiratory state of the user (for example, whether or not the user is in the above-described labored respiratory state), based on a detection result by the respiration detector 111

(that is, whether or not the user is in a respiratory arrest state) and a detection result by the body movement detector 112 (that is, whether or not the chest of the user is moving).

The storage 114 stores (accumulates) information indicating the respiratory state estimated by the respiratory state estimation module 113 (hereinafter, referred to as respiratory state information). The output module 115 outputs respiratory state information accumulated in the storage 114 during a sleeping period.

Figure 4:
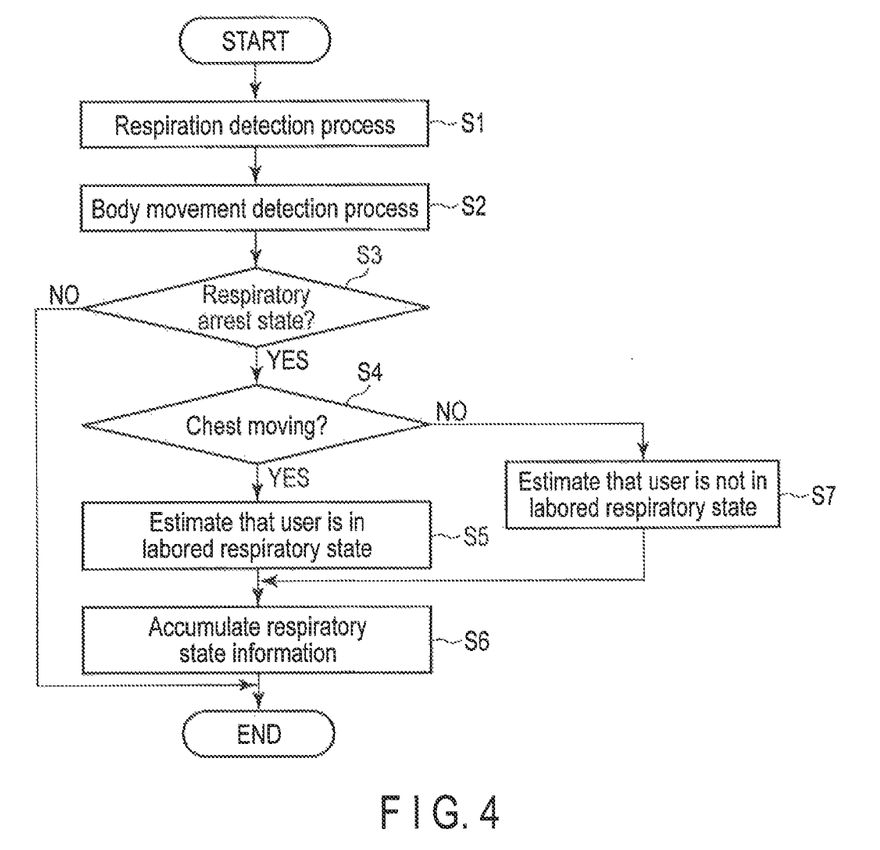
FIG. 4 is a flowchart showing an example of a procedure of the respiratory state estimation device according to the embodiment.

Next, a procedure of the respiratory state estimation device 10 according to the embodiment will be described with reference to the flowchart of FIG. 4. The processes shown in FIG. 4 are periodically performed during a sleeping period of the user.

First, the respiration detector 111 acquires a sound signal (internal sound signal, or external sound signal) measured by the microphone 106 used as the above-described respiratory measurement sensor. The respiration detector 111 performs a respiration detection process based on the acquired sound signal (step S1). In the respiration detection process, it is detected whether or not the user wearing the respiratory state estimation device 10 is in a respiratory arrest state.

In this case, the respiration detector 111 analyzes a frequency component or a waveform of the acquired sound signal. The respiration detector 111 detects that the user is in a respiratory arrest state (that is, respiration is arrested), when the above described respiratory sound signal is not extracted from the sound signal based on a result of the analysis. On the other hand, the respiration detector 111 detects that the user is not in a respiratory arrest state (that is, respiration is not arrested), when the respiratory sound signal is extracted from the sound signal based on a result of the analysis. The respiration detector 111 detects that the user is in a respiratory arrest state, when the respiratory sound signal is not extracted for a predetermined period (for example, ten seconds or more).

A result of the respiration detection process by the respiration detector 111 (hereinafter, referred to as a respiration detection result) is passed to the respiratory state estimation module 113. The respiration detection result in the case where the respiration detector 111 detects that the user is in a respiratory arrest state includes the time and date when it is detected that the user is in a respiratory arrest state, the duration of the respiratory arrest state, etc.

Next, the body movement detector 112 acquires an acceleration signal measured by the acceleration sensor 107 used as the above-described body movement measurement sensor. The body movement detector 112 performs a body movement detection process based on the acquired acceleration signal (step 22). In the body movement detection process, it is detected whether or not the chest of the user wearing the respiratory state estimation device 10 is moving.

In this case, the body movement detector 112 analyzes a waveform of the acquired acceleration signal. The body movement detector 112 detects that the chest of the user is moving, when an acceleration signal indicating a movement of the chest of the user is extracted from the acceleration signal based on a result of the analysis. On the other hand, it is detected that the chest of the user is not moving, when the acceleration signal indicating a movement of the chest of the user is not extracted from the acceleration signal based on a result of the analysis.

Figure 5:
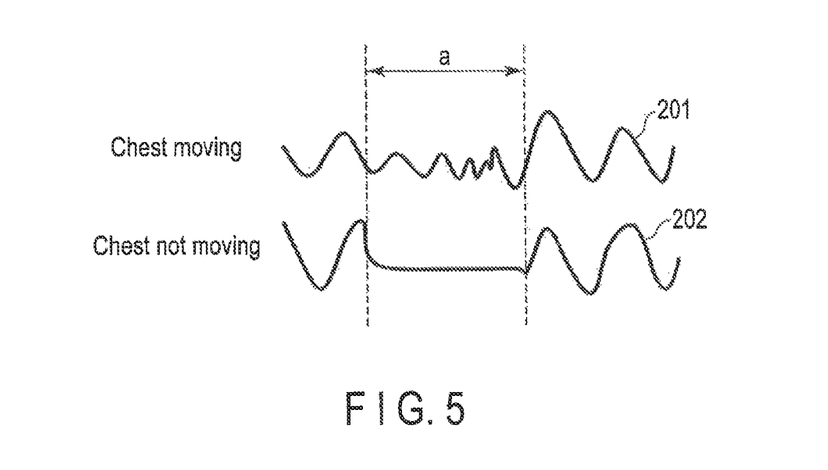
FIG. 5 is an illustration showing an example of an acceleration signal acquired by a body movement detector.

FIG. 5 shows an example of (a waveform of) an acceleration signal measured by the acceleration sensor 107. For example, a body movement waveform corresponding to respiration is detected from the waveform of the acceleration signal by a band-pass filter, etc., and acceleration due to gravity is detected by a low-pass filter. Here, regarding a period a shown in FIG. 5, when a waveform 201 of an acceleration signal is detected by the body movement detector 112, an acceleration signal indicating a movement of the chest of the user is extracted during the period a, and thus, it is detected that the chest is moving. On the other hand, when a waveform 202 of an acceleration signal is detected by the body movement detector 112, an acceleration signal indicating a movement of the chest of the user is not extracted during the period a, and thus, it is detected that the chest is not moving. The period a shown in FIG. 5 represents, for example, a period in which the user is in a respiratory arrest state.

A result of the body movement detection process by the body movement detector 112 (hereinafter referred to as a body movement detection result) is passed to the respiratory state estimation module 113. The body movement detection result includes, for example, the user's attitude (body position), in addition to whether or not the chest is moving. The user's attitude is, for example, a supine position, a prone position and a lateral position.

Here, since the acceleration sensor 107 of the embodiment is a triaxial acceleration sensor, as described above, the direction of acceleration due to gravity with respect to the respiratory state estimation device 10 can be calculated from an acceleration signal (acceleration due to gravity detected by the above-described low-pass filter) in each axial direction detected by the acceleration sensor 107.

The user's attitude included in the above-described body movement detection result can be estimated based on the direction of acceleration due to gravity with respect to the respiratory state estimation device 10, which is calculated in this manner.

More specifically, with respect to the attachment surface of the respiratory state estimation device 10, axes horizontal to the attachment surface and orthogonal each other are an x-axis and a y-axis, and an axis orthogonal to the x-axis and the y-axis (that is, an axis in a normal direction with respect to the attachment surface) is a z-axis. When the respiratory state estimation device 10 is attached to the chest of the user as shown in FIG. 1, the x-axis corresponds to an axis in a right and left direction of the user's body, the y-axis corresponds to an axis in an up and down direction of the user's body, and the z-axis corresponds to an axis in a forward and backward direction of the user's body, for example.

In this case, when the direction of acceleration due to gravity with respect to the respiratory state estimation device 10 is a backward direction of the user (that is, a back direction of the user) in the z-axis, the user's attitude is estimated to be a supine position. On the other hand, when the direction of acceleration due to gravity with respect to the respiratory state estimation device 10 is a forward direction of the user (that is, a front direction of the user) in the z-axis, the user's attitude is estimated to be a prone position. Further, when the direction of acceleration due to gravity with respect to the respiratory state estimation device 10 is an x-axis direction (that is, a right, and left direction of the user), the user's attitude is estimated to be a lateral position.

When the above-described processes of steps S1 and S2 are carried out the respiratory state estimation module 113 determines whether or not the user is in a respiratory arrest state, based on the respiration detection result (step S3).

When it is determined that the user is in a respiratory arrest state (YES in step S3), the respiratory state estimation module 113 determines whether or not the chest of the user is moving, based on the body movement detection result (step S4).

Here, when it is determined that the chest of the user is moving (YES in step S4), it can be estimated that the user performs the above-described labored respiration (that is, the user's respiratory state is a labored respiratory state), because the user is in a respiratory arrest state and the chest is moving (step S5).

In this case, the respiratory state estimation module 113 generates respiratory state information indicating that the user's respiratory state is a labored respiratory state, and accumulates (stores) the respiratory state information in the storage 114 (step S6). The respiratory state information indicating being a labored respiratory state indicates that the chest is moving in the above-described case where the user is in a respiratory arrest state, etc.

On the other hand, when it is determined that the chest of the user is not moving (NO in step S4). It can be estimated that the user does not perform labored respiration (that is, the user's respiratory state is not a labored respiratory state), because the user is in a respiratory arrest state, but the chest is not moving (step S7).

In this case, the respiratory state estimation module 113 generates respiratory state information indicating that the user's respiratory state is not a labored respiratory state, and the process of step S6 is carried out. The respiratory state information indicating not being a labored respiratory state indicates that the chest is not moving in the above-described case were the user is in a respiratory arrest state, etc.

When it is determined that the user is not in a respiratory arrest state in the above-described step S3 (NO in step S3), the processes of the respiratory state estimation device 10 are ended. It has been herein explained that the processes are ended when it is determined that the user is not in a respiratory arrest state. In this case, information indicating that the user is not in a respiratory arrest state (respiratory state information), for example, may be accumulated in the storage 114.

Since the above-described processes shown in FIG. 4 are periodically carried out during a sleeping period, of the user, a plurality of respiratory state information items generated during the sleeping period of the user are accumulated in the storage 114.

Figure 6:
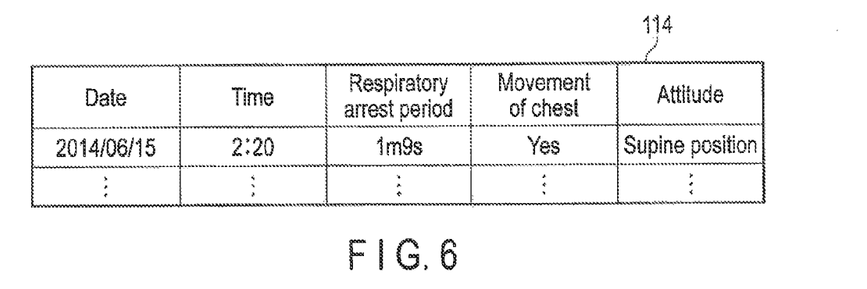
FIG. 6 is an illustration showing an example a data structure of respiratory state information accumulated in a storage.

Here, FIG. 6 shows an example of a data structure of respiratory state information accumulated in the storage 114. The respiratory state information stored in the storage 114 is information indicating the user's respiratory state estimated in the processes shown in FIG. 4, and includes the above-described respiration detection result and body movement detection result.

More specifically, the respiratory state information includes a date, a time, a respiratory arrest period, a movement of the chest, an attitude (sleeping attitude), etc., as shown in FIG. 6. The date and time indicate the date and time when it is detected that the user wearing the respiratory state estimation device 10 is in a respiratory arrest state. The respiratory arrest period indicates the duration of a respiratory arrest state (that is, a period in which the user is in a respiratory arrest state) in the case where it is detected that the user is in the respiratory arrest state. The movement of the chest indicates whether or not the chest is moving during the respiratory arrest period. The attitude indicates the user's attitude during the respiratory arrest period.

In the example shown in FIG. 6, the respiratory state information accumulated in the storage 114 includes the date "2014/06/15", the time "2:20", the respiratory arrest period "1m9s", the movement of the chest "Yes", and the attitude "supine position". According to the respiratory state information, it is indicated that the chest was moving during the respiratory arrest period of one minute, nine seconds, of a respiratory arrest state in a supine position detected at 2:20, Jun. 15, 2014.

The respiratory state information includes the movement of the chest "YES", and thus, is the above-described respiratory state information indicating being a labored respiratory state. On the other hand, although not shown in FIG. 6, respiratory state information including the movement of the chest "No" (that is, the chest was not moving) is respiratory state information indicating not being a labored respiratory state.

As described above, the respiratory state information accumulated in the storage 114 is output by the output module 115 to be presented to, for example, a patient (user) with sleep apnea syndrome or a doctor, etc. More specifically, the respiratory state information accumulated in the storage 114 is output to, for example, a display module (not shown) provided in the respiratory state estimation device 10, and is displayed in the display module.

A display example of respiratory state information in the respiratory state estimation device 10 will be hereinafter specifically described with reference to FIG. 7, in addition, since the respiratory state estimation device 10 according to the embodiment is a small, lightweight and thin device, an LED display lamp, for example, is used as the above-described display module.

Figure 7:
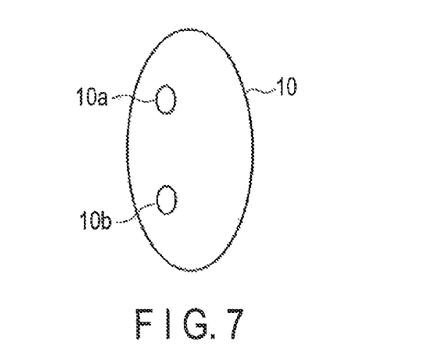
FIG. 7 is an illustration for specifically explaining a display example of respiratory state information in the respiratory state estimation device.

As shown in FIG. 7, (the surface of) the respiratory state estimation device 10 is provided with display lamps 10a and 10b. In the embodiment, respiratory state information is displayed by the display lamps 10a and 10b.

The display lamp 10a displays the number of times a respiratory arrest state is detected during a sleeping period (hereinafter, referred to as the number of respiratory arrests). In this case, the display lamp 10a lights in a color varying according to the number of respiratory arrests. More specifically, the display lamp 10a lights in green when the number of respiratory arrests is five to fourteen, in yellow when the number of respiratory arrests is fifteen to twenty-nine, and in orange when the number of respiratory arrests is greater than or equal to thirty. This enables the user or the doctor, etc., to easily ascertain the number of respiratory arrests during a sleeping period by the color of the display lamp 10a. The number of respiratory arrests can be acquired by counting the number of respiratory state information items accumulated in the storage 114 during a sleeping period.

The display lamp 10b displays whether or not the chest of the user is moving during a respiratory arrest period. More specifically, the display lamp 10b lights when the chest of the user is moving during a respiratory arrest period, and is extinguished when the chest of the user is not moving during the respiratory arrest period. This enables the user or the doctor, etc., to easily ascertain whether or not the chest of the user is moving (that is, whether or not labored respiration is performed) during a respiratory arrest period by the state (lighting or extinguished) of the display lamp 10b.

The respiratory state information accumulated in the storage 114 during a sleeping period may includes both respiratory state information including the movement of the chest "Yes" and respiratory state information including the movement of the chest "No". In this case, when the proportion of the respiratory state information indicating the movement of the chest "Yes" is greater than or equal to 60%, the display lamp 10b lights. On the other hand, when the proportion of the respiratory state information, including the movement of the chest "No" is greater than or equal to 60%, the display lamp to is extinguished.

When both the proportion of the respiratory state information including the movement of the chest "Yes" and the proportion of the respiratory state information including the movement of the chest "No" are less than 60% (for example, both the proportions are 50%), the display lamp 10*b* may be, for example, blinked to show that it is hard to determine whether or not the chest is moving.

Although the case where the respiratory state information accumulated in the storage 114 is displayed by the display lamps 10*a* and 10*b* has been herein described, the respiratory state information can also be displayed by characters, etc., when the respiratory state estimation device 10 is provided with a small display, etc.

In addition, since the respiratory state estimation device 10 is a small, lightweight and thin device as described above, the content that can be displayed is limited when the respiratory state information is displayed in the respiratory state estimation device 10. Thus, for example, the respiratory state information accumulated in the storage 114 can also be transmitted (output) from the output module 115 to an external device (for example, as smart phone, a tablet computer, or a PC) to be displayed in the external device, in this case, the respiratory state information is transmitted to the external device through, for example, the above-described Bluetooth module 108. The respiratory state information may be transmitted through a wireless LAN, etc.

A display example of displaying respiratory state information output by (the output module 115 included in) the respiratory state estimation device 10 in the external device will be hereinafter specifically described. First to third display examples will be described herein.

Figure 8:
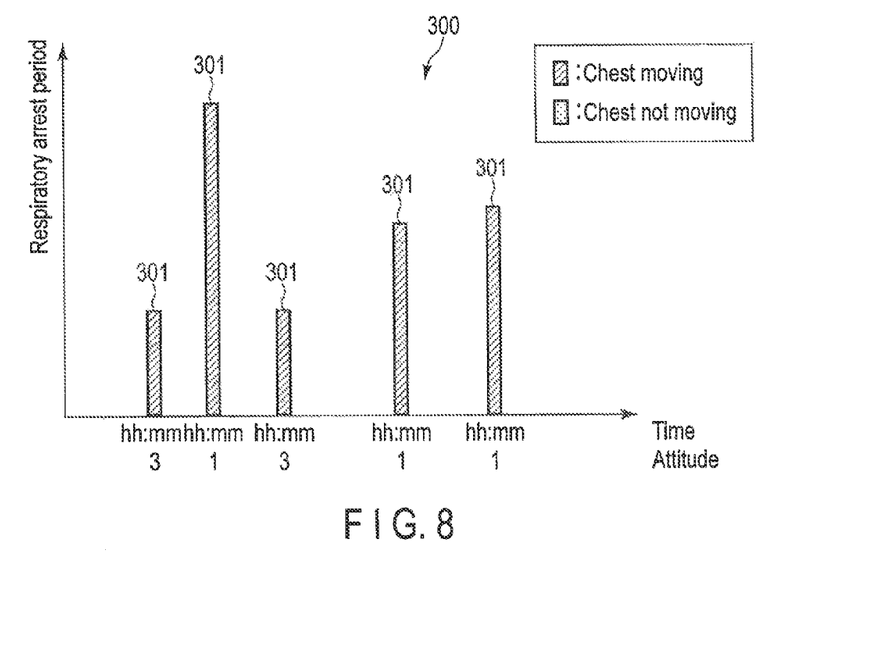
FIG. 8 is an illustration showing a first display example of displaying respiratory state information output by the respiratory state estimation device in an external device.

First, FIG. 8 shows the first display example of respiratory state information. As shown in FIG. 8, in the first display example, respiratory state information is displayed as a graph (bar graph) 300, in the graph 300, a vertical axis indicates a respiratory arrest period, and a horizontal axis indicates a time.

Specifically, each rectangular region 301 in the shape of a bar in the graph 300 indicates a time at which a respiratory arrest state is detected and the duration of the respiratory arrest state (that is, a respiratory arrest period). Further, each rectangular region 301 is colored, and its color indicates whether or not the chest is moving. More specifically, when a rectangular region 301 is colored in blue, it is indicated that the chest was moving during a respiratory arrest period indicated by the rectangular region 301. On the other hand, when a rectangular region 301 is colored in red, it is indicated that the chest was not moving during a respiratory arrest period indicated by the rectangular region 301. In the example shown in FIG. 8, all the rectangular regions 301 are colored in blue (that is, the chest was moving during all the respiratory arrest periods).

Furthermore, an attitude at a time at which a respiratory arrest state is detected (that is, during a respiratory arrest period) is shown below the time in FIG. 8. In the example shown in FIG. 8, each attitude is represented by a number assigned to them. More specifically, "1" represents a supine position, "2" represents a prone position, and "3" represents a lateral position.

Since the above-described graph 300 as shown in FIG. 8 indicates a time at which a respiratory arrest state is detected, a respiratory arrest period, the number of respiratory arrests, whether or not the chest is moving, an attitude, etc., during a sleeping period, the user or the doctor, etc., can easily ascertain whether or not the above-described labored respiration is performed.

Figure 9:
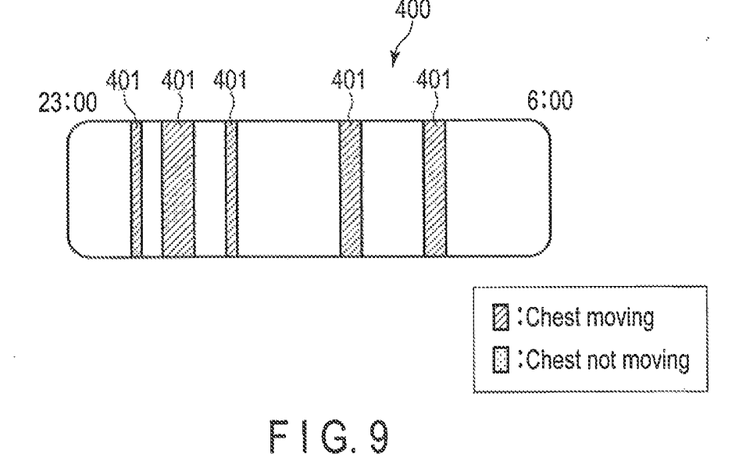
FIG. 9 is an illustration showing a second display example of displaying respiratory state information output by the respiratory state estimation device in the external device.

Next, FIG. 9 shows the second display example of respiratory state information. As shown in FIG. 9, in the second display example, respiratory state information is displayed as a graph 400 differing from the graph in FIG. 8. Each region 401 in the graph 400 indicates a respiratory arrest period during a sleeping period (here, 23:00 to 6:00) by the width, in addition, the color of each region 401 indicates whether or not the chest is moving. Because a specific example of indicating whether or not the chest is moving by the color is the same as in FIG. 8, a detailed explanation thereof is omitted herein.

Since the above-described graph 400 shown in FIG. 9 indicates a respiratory arrest period, the number of respiratory arrests, whether or not the chest is moving, etc., during a sleeping period, the user or the doctor, etc., can easily ascertain whether or not the above-described labored respiration is performed.

Figure 10:
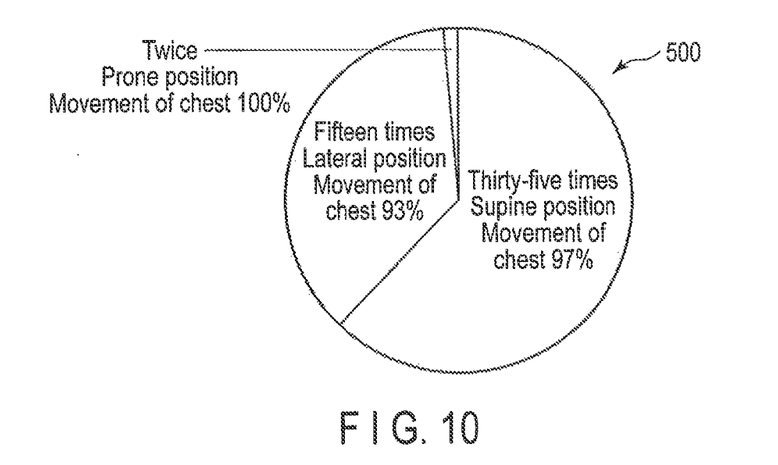
FIG. 10 is an illustration showing a third display example of displaying respiratory state information output by the respiratory state estimation device in the external device.

Next, FIG. 10 shows the third display example of respiratory state information. As shown in FIG. 10, in the third example, respiratory state information is displayed as a graph (circle graph) 500. In the graph 500, the proportion of the number of respiratory arrests in each attitude of the user to the number of respiratory arrests during a sleeping period is indicated by the area it covers in the graph 500. Moreover, in the graph 500, the proportion of the movement of the chest in each attitude of the user is indicated by numerical values (%). The proportion of the movement of the chest is the proportion of respiratory arrest states (the number of respiratory arrests) in which it is detected that the chest is moving to the respiratory arrest states (the number of respiratory arrests) detected in each attitude of the user.

More specifically, in the example shown in FIG. 10, it is indicated that the number of respiratory arrests in the case where the user's attitude is a supine position is thirty-five, and the proportion of respiratory arrest states in which the chest is moving to the thirty-five respiratory arrest states is 97%. Similarly, it is indicated that the number of respiratory arrests in the case where the user's attitude is a lateral position is fifteen, and the proportion of respiratory arrest states in which the chest is moving to the fifteen respiratory arrest states is 93%. Moreover, it is indicated that the number of respiratory arrest states in the case where the user's attitude is a prone position is two, and the proportion of respiratory arrest states in which the chest is moving to the two respiratory arrest states is 100%.

Since the above-described graph 500 as shown in FIG. 10 indicates the number of respiratory arrests, whether or not the chest is moving, an attitude, etc., during a sleeping period, the user or the doctor, etc., can easily ascertain whether or not the above-described labored respiration is performed.

Although the case where respiratory state information output from the respiratory state estimation device 10 is displayed as a graph has been mainly described with reference to FIG. 6 to FIG. 10, the respiratory state information can also be displayed as a file. Furthermore, although it has been herein explained that respiratory state information accumulated during a sleeping period of one day is displayed, respiratory state information of each date can also be displayed in a form in which respiratory state information items can be compared as shown in FIG. 11, for example, to confirm the effect of the treatment for sleep apnea syndrome.

Figure 11:
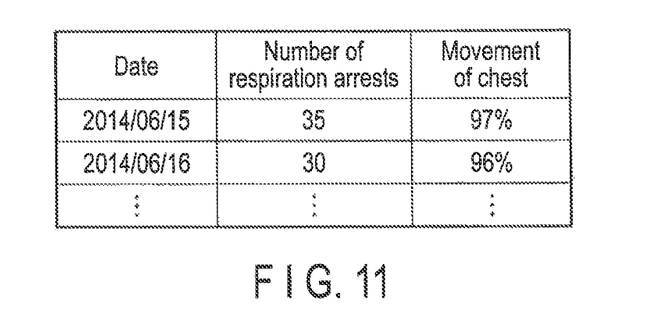
FIG. 11 is an illustration showing an example of displaying respiratory state information of each date in a form in which respiratory state information items can be compared.

In FIG. 11, the number of respiratory arrests and the proportion of the movement of the chest of each date are indicated.

Moreover, it has been herein explained that whether or not the chest is moving during a respiratory arrest period, etc., are displayed in the respiratory state estimation device 10 or the external device, etc. However, when the chest is moving during, a respiratory arrest period, it may be displayed that the user's respiratory state is a labored respiratory state, and when the chest is not moving during the respiratory arrest period, it may be displayed that the user's respiratory state is not a labored respiratory state. That is, in the embodiment, respiratory state information may be displayed in forms other than those described above, as long as the user or the doctor, etc., can ascertain whether labored respiration is performed during a sleeping period.

Furthermore, although it has been herein explained that respiratory state information is directly transmitted (output) to the external device, the respiratory state information can also be displayed in an external device such as a smartphone, after being transmitted to, for example, a server device functioning as a cloud server which provides a cloud computing service through a wireless LAN, etc., and being accumulated in the server device.

As described above, in the embodiment, the user's respiratory state is estimated based on a result of detecting whether or not the user is in a respiratory arrest state and a result of detecting whether or not the trunk of the user is moving (for example, the chest is moving), and respiratory state information indicating the estimated respiratory state is output, whereby information helpful in the diagnosis of a pathology related to respiration during sleep, for example, sleep apnea syndrome, can be provided.

That in the embodiment, the user's respiratory state is estimated to be a labored respiratory state, when it is detected that the user is in a respiratory arrest state and it is detected that the chest of the user is moving, and the user's respiratory state is not estimated to be a labored respiratory state, when it is detected that the user is in a respiratory arrest state and it is detected that the chest of the user is not moving. Accordingly, in the embodiment, since respiratory state information indicating being a labored respiratory state or respiratory state information indicating not being a labored respiratory state can be output, information (respiratory state information) helpful for a doctor, etc., to discriminate between obstructive SAS and central SAS, for example, can be provided.

In addition, in the embodiment, respiratory state information including the number of respiratory arrests and whether or not the chest of the user is moving during a respiratory arrest period is displayed by the display lamps 10a and 10b, etc., whereby the user or the doctor, etc., can easily ascertain the respiratory state information (that is, whether labored respiration is performed, etc.) by the respiratory state estimation device 10 only.

Moreover, in the embodiment, respiratory state information including a time at which it is detected that the user is in a respiratory arrest state, a period in which the user is in the respiratory arrest state, and whether or not the chest of the user is moving during the period in which the user is in the respiratory arrest state is output to the external device, whereby the user or the doctor, etc., can ascertain the respiratory state information in more detail than in the case where the respiratory State information is displayed by the respiratory state estimation device 10.

In addition, in the embodiment, although it has been explained that the microphone 106 is used as the respiratory measurement sensor, other sensors may be used as the respiratory measurement sensor. Examples of a sensor which can be used as the respiratory measurement sensor will be hereinafter briefly described.

Figure 12:
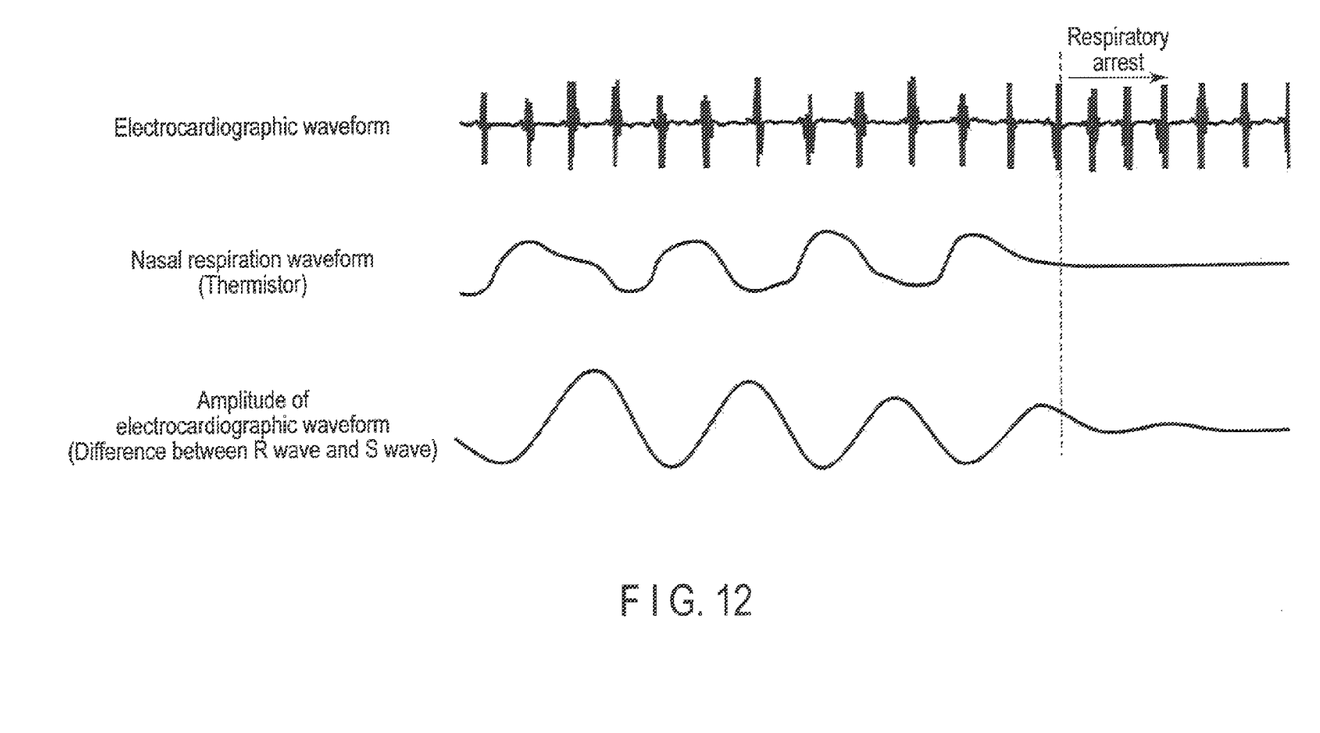
FIG. 12 is an illustration for explaining a case where an electrocardiographic sensor is used as a respiratory measurement sensor.

First, for example, an electrocardiographic sensor which measures an electrocardiographic signal indicating an electrocardiographic waveform (electrocardiogram) of the user can be used as the respiratory measurement sensor. Here, as shown in FIG. 12, (an electrocardiographic signal indicating) an electrocardiographic waveform is measured by the electrocardiographic sensor. When a difference between an R wave and an S wave in an electrocardiogram is defined as the amplitude of the electrocardiographic waveform, the amplitude assumes the same waveform as a nasal respiration waveform measured by a thermistor used by being fixed in front of a nose or a mouth or being inserted into nostrils. Thus, also in the case where the electrocardiographic sensor is used as the respiratory measurement sensor, it can be detected whether or not the user is in a respiratory arrest state, based on the amplitude (or a base line) of the electrocardiographic waveform.

Figure 13:
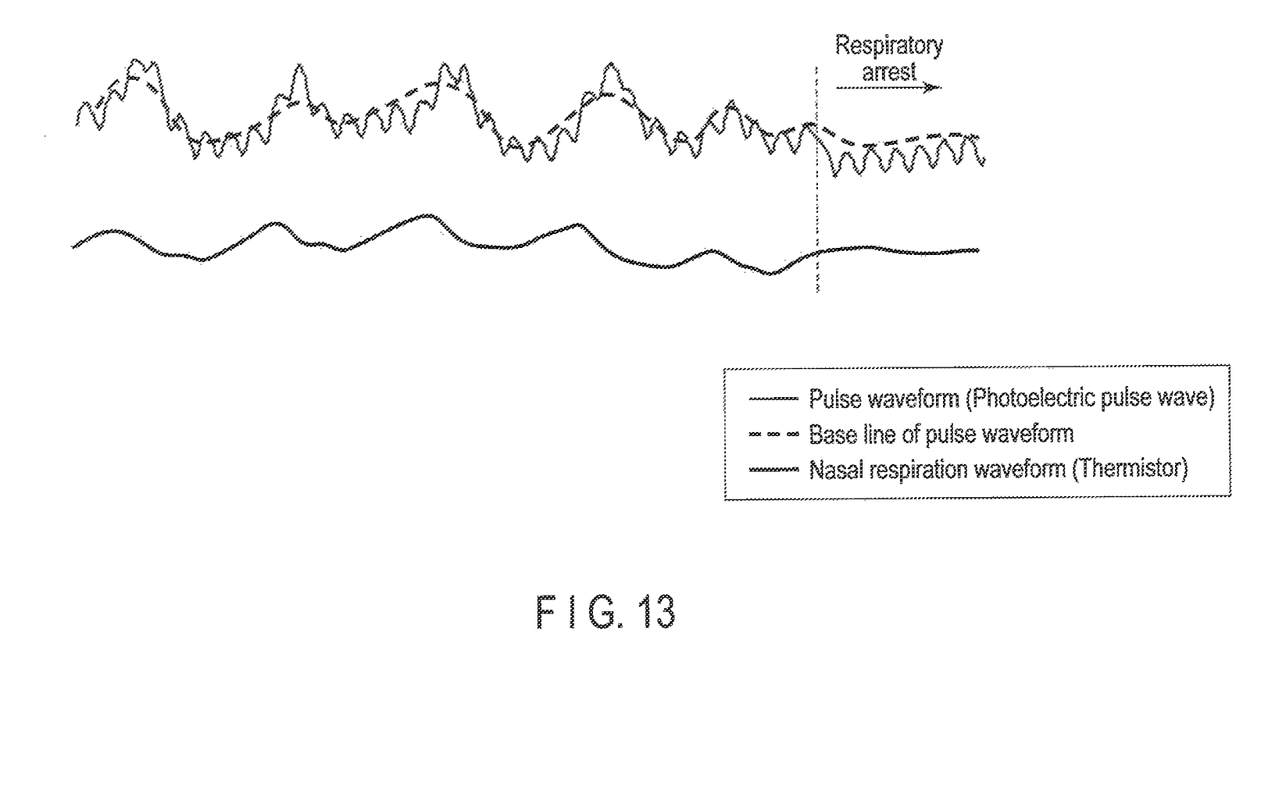
FIG. 13 is an illustration for explaining a case where a pulse sensor is used as the respiratory measurement sensor.

In addition, for example, a pulse sensor of a photoelectric pulse method which measures a pulse signal indicating a pulse waveform of the user can be used as the respiratory measurement sensor. Here, as shown in FIG. 13, a base-line waveform of a pulse waveform (solid line) measured by such a pulse sensor assumes the same waveform as the above-described nasal respiration waveform (wide line). More specifically, when the pulse sensor of a photoelectric pulse method is attached to the chest, a pulse wave assumes a waveform as indicated by the solid line, a base line (broken line) of the pulse waveform assumes the same waveform as a respiration waveform. The base-line waveform of the pulse waveform can be detected by using a low-pass filter. Therefore, also in the case where the pulse sensor is used as the respiratory measurement sensor, it can be detected whether or not the user is in a respiratory arrest state, based on the base line (waveform) of the pulse waveform. The base-line waveform of the pulse waveform can be acquired by the low-pass filter.

Moreover, except for the above-described electrocardiographic sensor and, pulse sensor, an arterial blood oxygen saturation measure (SpO2 sensor) which measures arterial blood oxygen saturation (SpO2) of the user may be used as the respiratory measurement sensor to detect whether or not the user is in a respiratory arrest state, based on the arterial blood oxygen saturation. The arterial blood oxygen saturation measure is, for example, a reflective pulse oximeter.

In addition, in the embodiment, it has been explained that the acceleration sensor 107 is used as the body movement measurement sensor. However, for example, a noise produced in accordance with a movement of the chest of the user included, in a signal (for example, a sound signal) measured by the above-described respiratory measurement sensor may be measured to detect whether or not the chest of the user is moving, based on the noise.

The above-described respiratory measurement sensor and body movement measurement sensor may be a combination of sensors.

In addition, the respiratory state estimation device 10 according to the embodiment can detect that the user is in a respiratory arrest state as described above. Therefore, for example, to avoid a respiratory arrest state, it is also possible to output (generate) an alarm (alarm sound) in the respiratory state estimation device 10, when a respiratory arrest state is detected, or stimulate the user through the respiratory state estimation device 10, when the respiratory arrest state continues for a predetermined period (for example, one minute) or more.

Moreover, a respiratory arrest state often occurs when the user's attitude (sleeping attitude) is a supine position. Thus, for example, when the user's attitude is a supine position and pulmonary respiration is performed (that is, the chest is moving), it is also possible to urge the user to sleep in a lateral position in cooperation with an external device by transmitting information to the external device. More specifically, the user can be urged to sleep in a lateral position by outputting a sound from, for example, the right or the left of the user in cooperation with a speaker. Further, it is similarly possible to urge the user to sleep in a lateral position in cooperation with bedding (for example, a device which controls an electric bed, etc.) by stimulating the left or the right of the user, changing the temperature of the left or the right of the user, or deforming the bedding. Moreover, in cooperation with a lighting fixture (light), a light, can also be flashed from the left or the right of the user.

Since the above-described processing of the embodiment can be implemented by a computer program, the same advantages as those of the embodiment can be easily achieved by installing the computer program in a computer and executing the computer program.

Moreover, in the embodiment, it has been explained that each of the portions 111 to 115 is included in the respiratory state estimation device 10, which is a small, lightweight and thin device which is attached to the user when used. However, the processing of each of the portions 111 to 115 may also be executed in, for example, the external device, based on an output signal from the respiratory measurement sensor and the body movement measurement sensor which are provided in a device which is attached to the user.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A respiratory state estimation device attached to a user during sleep when used, comprising:
    a respiratory measurement module configured to measure a first signal related to a respiratory fluctuation of the user;
    a body movement measurement module configured to measure a second signal related to a movement of a trunk of the user;
    a respiration detector configured to detect whether or not the user is in a respiratory arrest state, based on the first signal measured by the respiratory measurement module;
    a body movement detector configured to detect whether or not the trunk of the user is moving, based on the second signal measured by the body movement measurement module;
    an estimation module configured to estimate a respiratory state of the user, based on a detection result by the respiration detector and a detection result by the body movement detector; and
    an output module configured to output respiratory state information indicating the estimated respiratory state, wherein
    the body movement measurement module is configured to measure a noise produced in accordance with the movement of the trunk of the user, the noise being included in the first signal measured by the respiratory measurement module, and
    the body movement detector is configured to detect whether or not the trunk of the user is moving, based on the noise measured by the body movement measurement module.

2. The device of claim 1, wherein the estimation module is further configured to:
    estimate that the respiratory state of the user is a labored respiratory state, when the respiration detector detects that the user is in the respiratory arrest state and the body movement detector detects that the trunk of the user is moving, and
    estimate that the respiratory state of the user is not the labored respiratory state, when the respiration detector detects that the user is in the respiratory arrest state and the body movement detector detects that the trunk of the user is not moving.

3. The device of claim 2, further comprising a display module, wherein
    the respiratory state information includes the number of times it is detected that the user is in the respiratory arrest state during the sleep and whether or not the trunk of the user is moving during a period in which the user is in the respiratory arrest state, and
    the display module is configured to display the respiratory state information output by the output module.

4. The device of claim 2, wherein
    the respiratory state information includes a time at which it is detected that the user is in the respiratory arrest state, a period in which the user is in the respiratory arrest state, and whether or not the trunk of the user is moving during the period in which the user is in the respiratory arrest state, and
    the output module is further configured to output the respiratory state information to an external device.

5. The device of claim 1, wherein
    the respiratory measurement module includes a microphone configured to measure a respiratory sound signal indicating a respiratory sound produced in accordance with the respiratory state of the user, and
    the respiration detector is further configured to detect whether or not the user is in the respiratory arrest state, based on a frequency component or a waveform of the respiratory sound signal measured by the microphone.

6. The device of claim 1, wherein
    the respiratory measurement module includes an electrocardiographic sensor configured to measure an electrocardiographic signal indicating an electrocardiographic waveform of the user, and
    the respiration detector is further configured to detect whether or not the user is in the respiratory arrest state, based on amplitude of the electrocardiographic waveform indicated by the electrocardiographic signal measured by the electrocardiographic sensor.

7. The device of claim 1, wherein
    the respiratory measurement module includes a pulse sensor configured to measure a pulse signal indicating a pulse waveform of the user, and
    the respiration detector is further configured to detect whether or not the user is in the respiratory arrest state, based on a base line of the pulse waveform indicated by the pulse signal measured by the pulse sensor.

8. The device of claim 1, wherein
the respiratory measurement module includes an arterial blood oxygen saturation measure configured to measure arterial blood oxygen saturation of the user, and
the respiration detector is further configured to detect whether or not the user is in the respiratory arrest state, based on the arterial blood oxygen saturation measured by the arterial blood oxygen saturation measure.

9. The device of claim 1, wherein
the body movement measurement module includes an acceleration sensor configured to measure an acceleration signal indicating acceleration produced in accordance with a movement of a chest of the user, and
the body movement detector is further configured to detect whether or not the trunk of the user is moving, based on a waveform of the acceleration signal measured by the acceleration sensor.

10. A respiratory state estimation method executed by a respiratory state estimation device comprising a respiratory measurement module configured to measure a first signal related to a respiratory fluctuation of a user during sleep and a body movement measurement module configured to measure a second signal related to a movement of a trunk of the user,
the method comprising:
detecting whether or not the user is in a respiratory arrest state, based on the first signal measured by the respiratory measurement module;
detecting whether or not the trunk of the user is moving, based on the second signal measured by the body movement measurement module;
estimating a respiratory state of the user, based on a result of detecting whether or not the user is in the respiratory arrest state and a result of detecting whether or not the trunk of the user is moving; and
outputting respiratory state information indicating the estimated respiratory state, wherein
the body movement measurement module is configured to measure a noise produced in accordance with the movement of the trunk of the user, the noise being included in the first signal measured by the respiratory measurement module, and
whether or not the trunk of the user is moving is detected based on the noise measured by the body movement measurement module.

11. A non-transitory computer-readable storage medium having stored thereon a computer program which is executable by a computer of a respiratory state estimation device comprising a respiratory measurement module configured to measure a first signal related to a respiratory fluctuation of a user during sleep and a body movement measurement module configured to measure a second signal related to a movement of a trunk of the user, the computer program comprising instructions capable of causing the computer to execute functions of:
detecting whether or not the user is in a respiratory arrest state, based on the first signal measured by the respiratory measurement module;
detecting whether or not the trunk of the user is moving, based on the second signal measured by the body movement measurement module;
estimating a respiratory state of the user, based on a result of detecting whether or not the user is in the respiratory arrest state and a result of detecting whether or not the trunk of the user is moving; and
outputting respiratory state information indicating the estimated respiratory state, wherein
the body movement measurement module is configured to measure a noise produced in accordance with the movement of the trunk of the user, the noise being included in the first signal measured by the respiratory measurement module, and
whether or not the trunk of the user is moving is detected based on the noise measured by the body movement measurement module.

\* \* \* \* \*